US007934412B2

(12) United States Patent
Prince

(10) Patent No.: US 7,934,412 B2
(45) Date of Patent: May 3, 2011

(54) INNOVATIVE GAS MONITORING WITH SPACIAL AND TEMPORAL ANALYSIS

(75) Inventor: Dennis Scott Prince, Edmonton (CA)

(73) Assignee: Airdar Inc., Edmonton (CA)

( * ) Notice: Subject to any disclaimer, the term of this patent is extended or adjusted under 35 U.S.C. 154(b) by 0 days.

(21) Appl. No.: 12/261,443

(22) Filed: Oct. 30, 2008

(65) Prior Publication Data

US 2009/0139299 A1 Jun. 4, 2009

(51) Int. Cl.
*G01N 31/00* (2006.01)

(52) U.S. Cl. ........................................................ 73/1.07

(58) Field of Classification Search ................. 73/31.02, 73/23.31; 702/100
See application file for complete search history.

(56) References Cited

U.S. PATENT DOCUMENTS 4,127,780 A 11/1978 Kimbell .......................... 250/55
4,135,092 A 1/1979 Milly .............................. 250/34
4,204,121 A 5/1980 Milly .............................. 250/34
4,785,658 A * 11/1988 Jackson ....................... 73/31.01
5,099,437 A 3/1992 Weber ............................. 702/18
5,106,756 A 4/1992 Zaromb .......................... 436/16
5,347,285 A * 9/1994 MacDoran et al. ...... 342/357.12
5,386,373 A 1/1995 Keeler ............................ 700/26
5,604,299 A 2/1997 Cobb ................................ 73/31
5,719,396 A 2/1998 Jack et al. ....................... 250/33
5,726,450 A 3/1998 Peterson et al. ................ 250/33
5,832,411 A 11/1998 Schatzmann et al. ........... 702/23
5,879,943 A 3/1999 Ando et al. ...................... 436/41
5,918,257 A 6/1999 Mifsud et al. .................. 73/23.3
6,148,656 A * 11/2000 Breton ......................... 73/23.31
6,734,824 B2 5/2004 Herman .......................... 342/46
6,895,335 B2 5/2005 Archibald et al. ................ 702/2
2002/0169557 A1 11/2002 Gilbert et al. ..................... 702/3
2009/0139299 A1* 6/2009 Prince ........................... 73/1.06

FOREIGN PATENT DOCUMENTS

EP 448360 A1 * 9/1991
JP 11118701 A 4/1999

OTHER PUBLICATIONS

The Alberta Oil Sands Community Exposure and Health Effects Assessment Program: Technical Report (Dr. Petros Koutrakis et al), Aug. 2000, pp. 206-217.
ERCB. 1990. Field Measurement Progam: Atmospheric Dispersion Tracer Study Under Stable Conditions and Meterology Study. ERCB Report 90-B vol. 1. Calgary, Alberta.
ERCB. 1990. Field Measurement Program: Atmospheric Dispersion Tracer Study Under Stable Condition and Meterology Study. ECRB Report 90-B vol. 1. Calgary, Alberta. The relevant passages and relevant figures appear at paragraphs 4.4.2 and 4.2.1.

* cited by examiner

*Primary Examiner* — Hezron Williams
*Assistant Examiner* — Tamiko D Bellamy
(74) *Attorney, Agent, or Firm* — Bennett Jones LLP

(57) ABSTRACT

The present invention relates to the monitoring of gas concentrations possible in very low ranges (i.e., low ppb and even ppt ranges) and especially use thereof in environmental monitoring, exposure assessment, bomb detection, and health studies. The invention can use a spatial and temporal assessment of gas concentrations that enables the sources of the gas in question to be located and identified which is useful in environmental and health field but can also be applied to other fields an example of which is detecting and locating explosives. This technology can uses small, light weight, and low power components that allow for the monitor to be portable and even worn on a person as a personal monitor. This technology can be used in a stationary monitors as well.

18 Claims, 17 Drawing Sheets

Figure showing sensor array and source location technique.

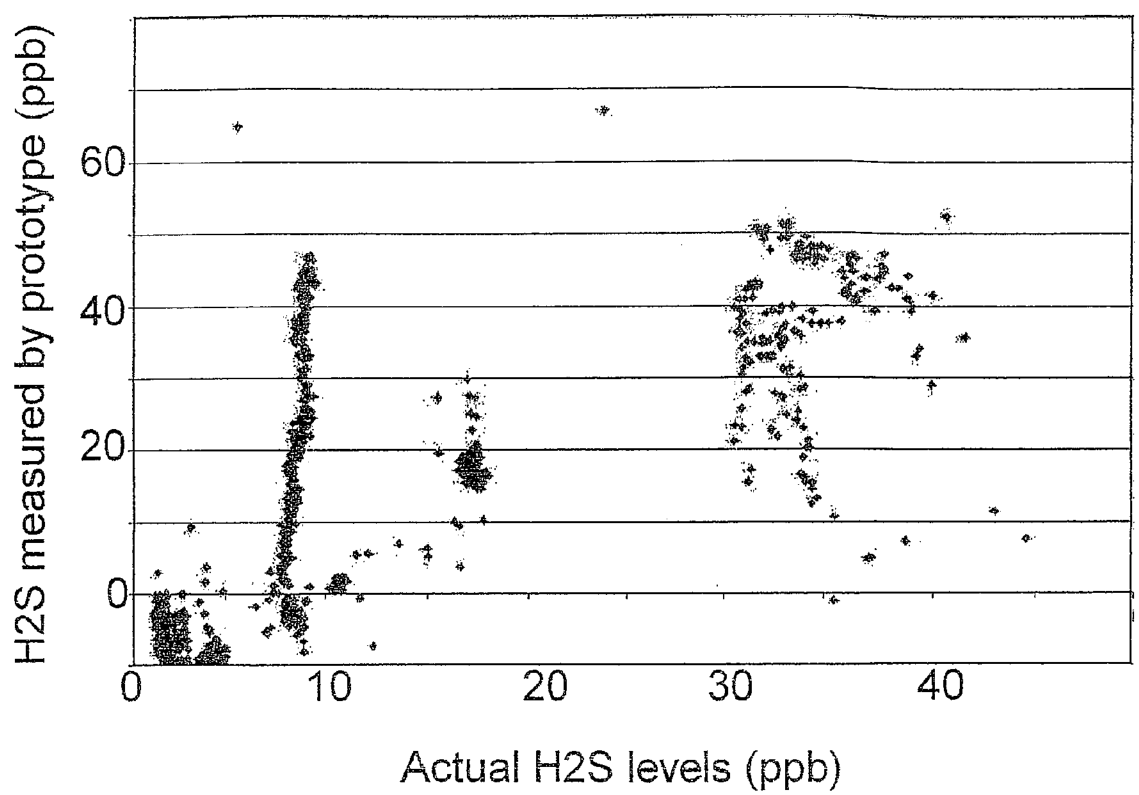
Figure 1: Raw Data

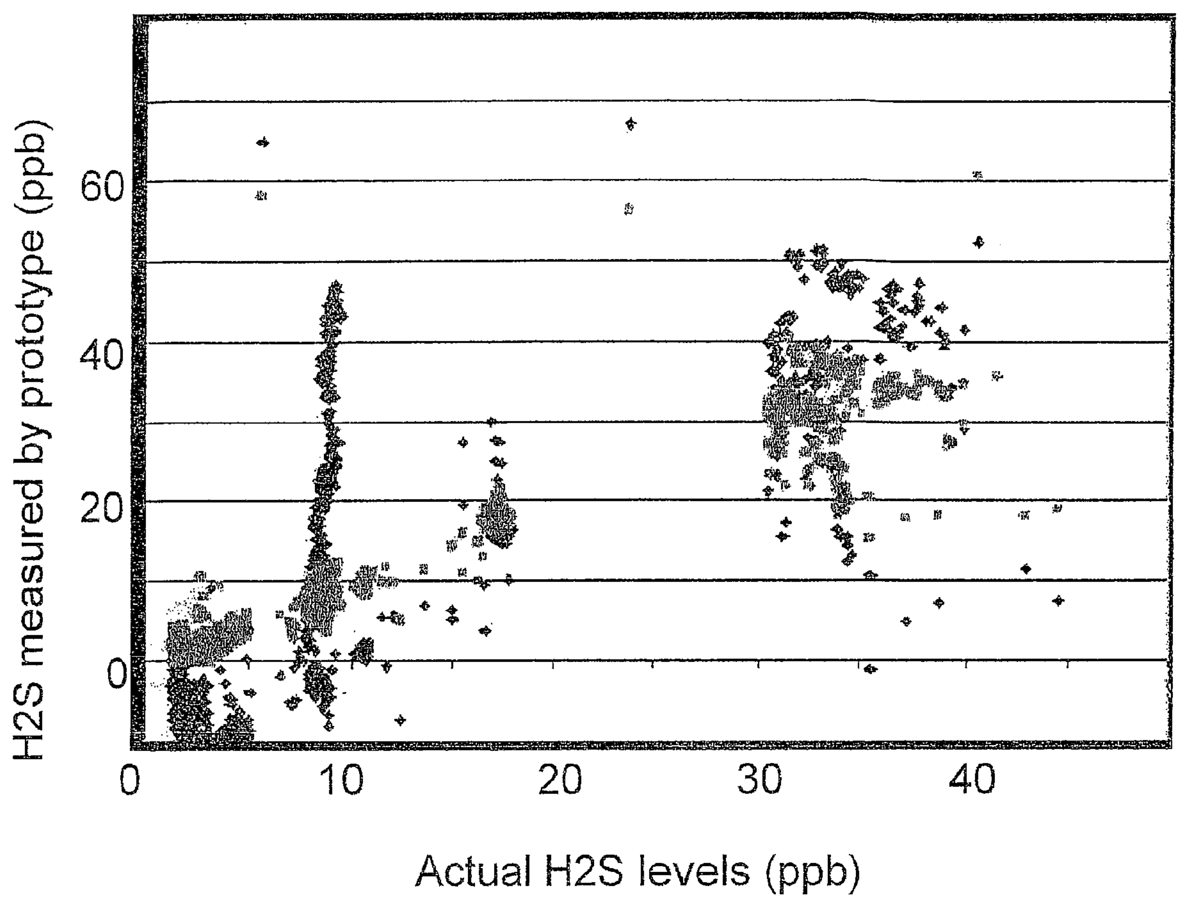
Figure 2: Baseline corrected output

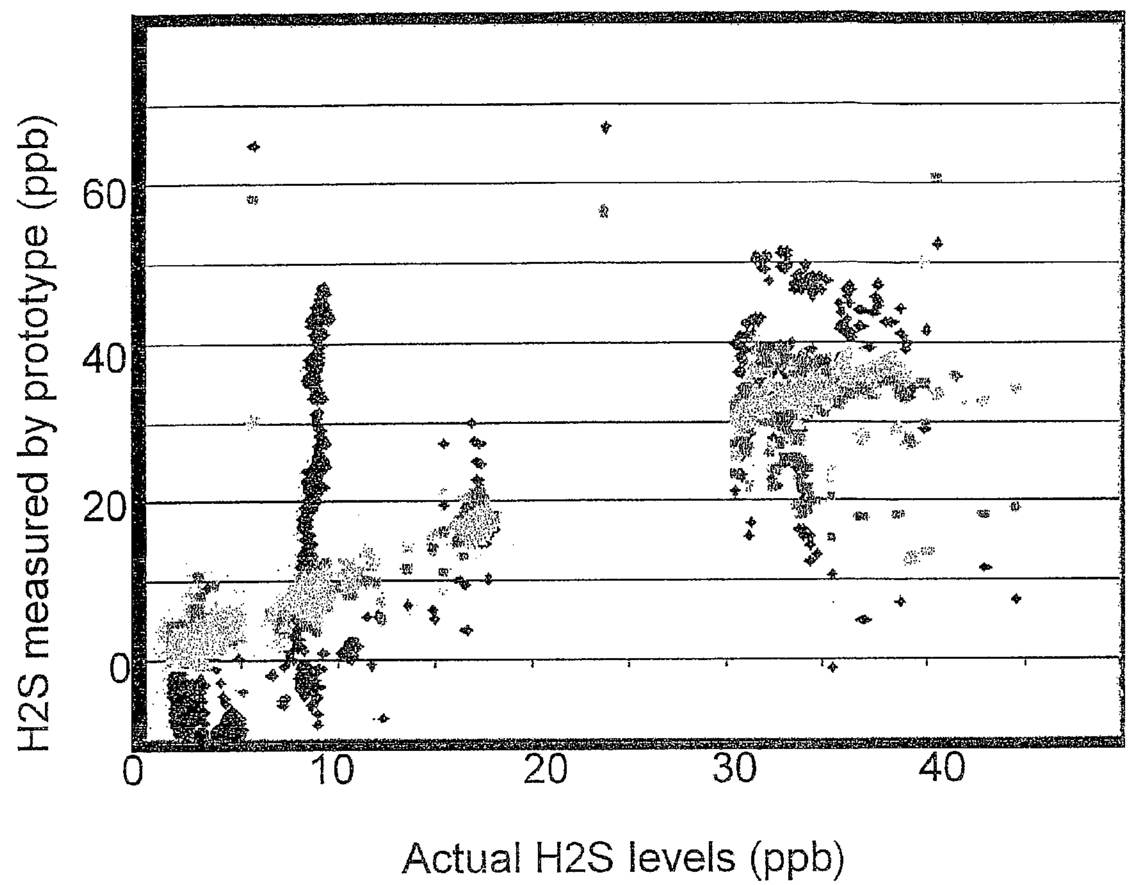
Figure 3: Sensitivity corrected output

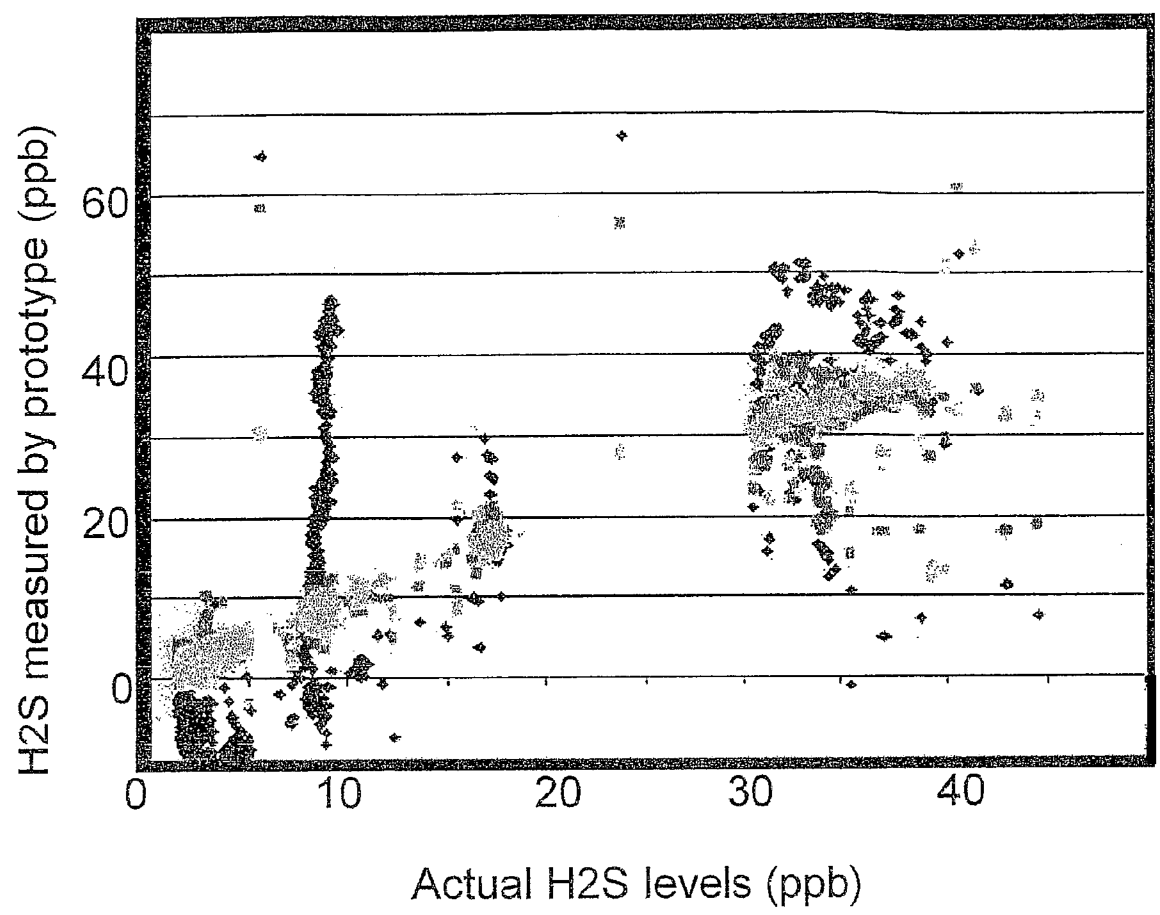
Figure 4: Multiple sensors

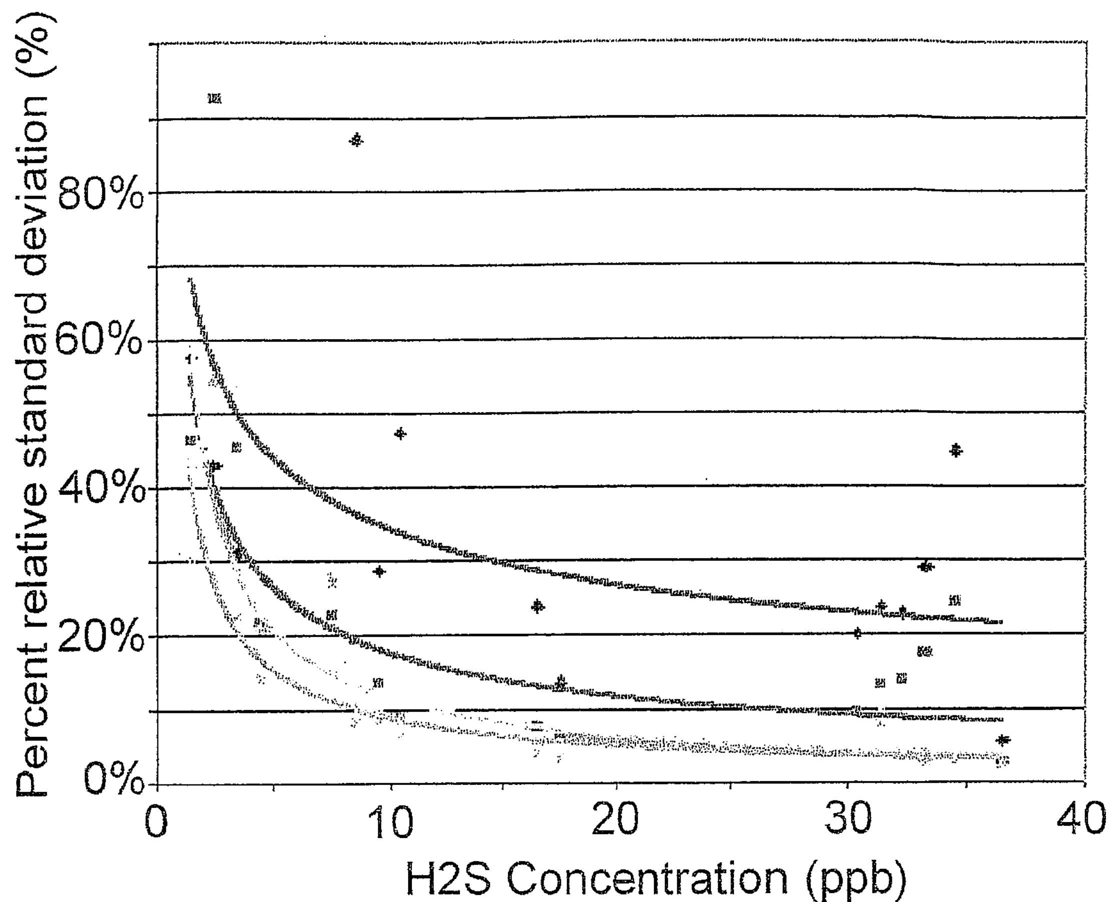
Figure 5: Improvement in monitor precision achieved by methodologies
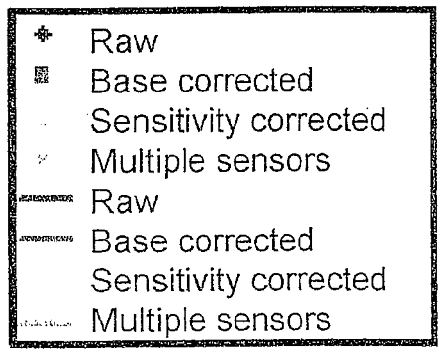

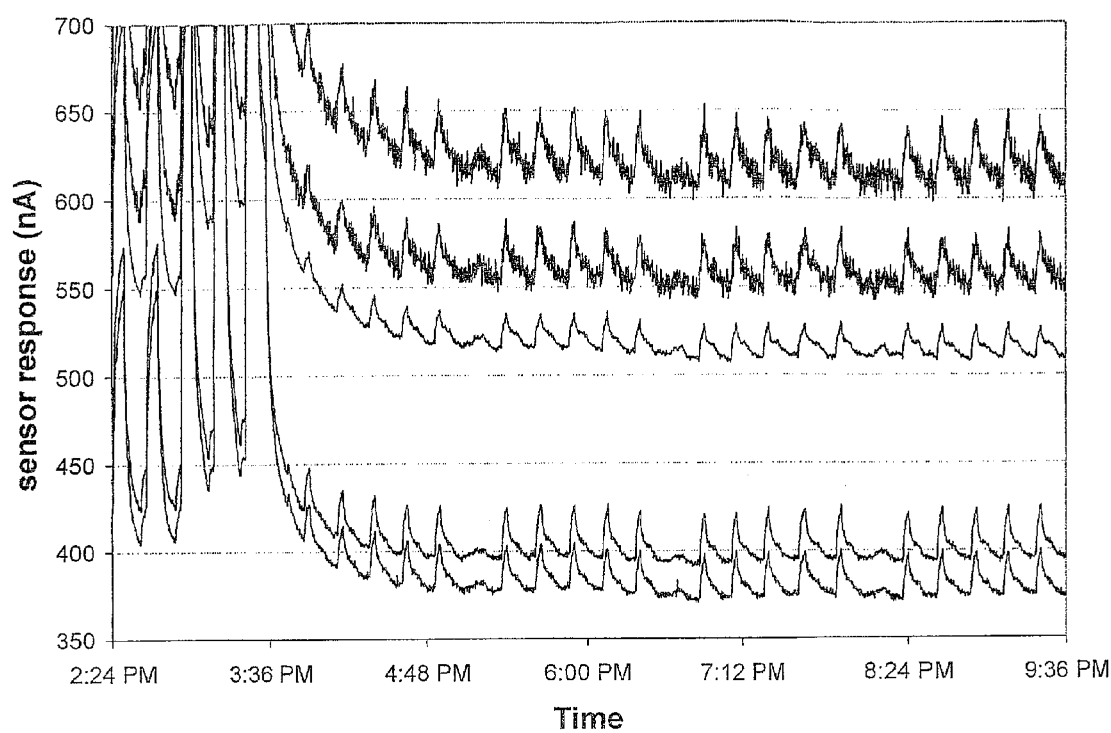
Figure 6: Sample output of five sensors cycling through the modes of operation

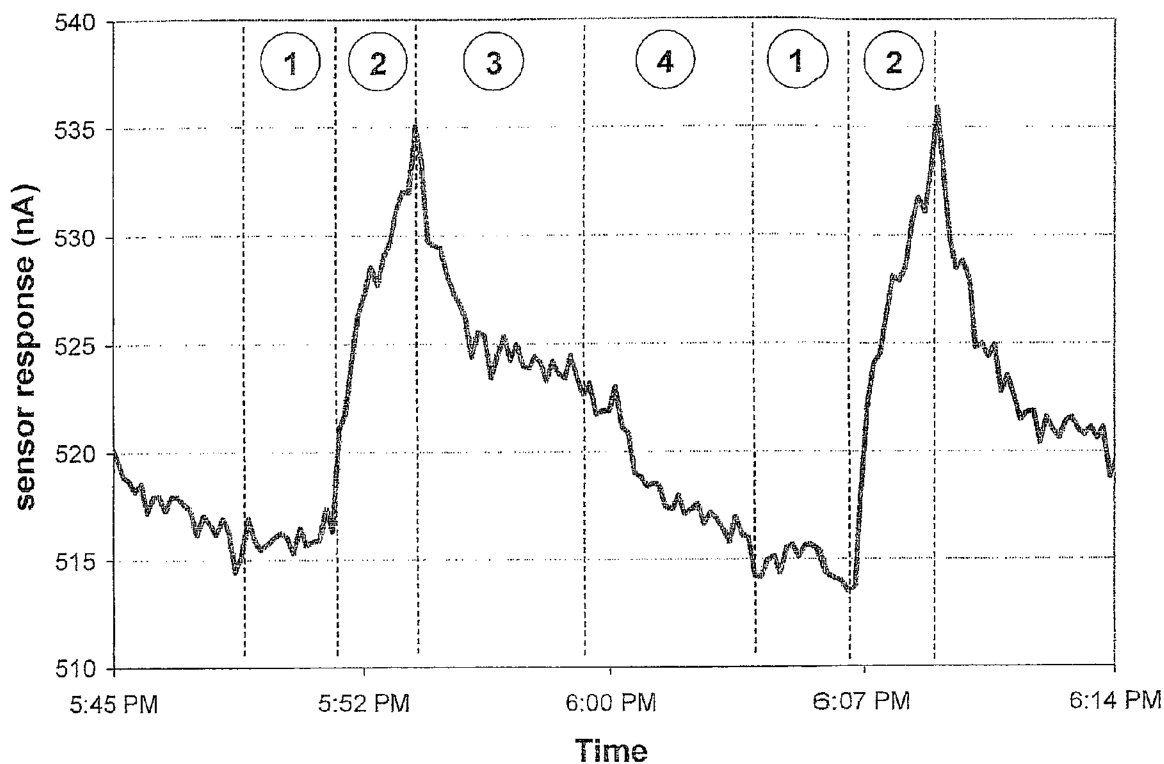
Figure 7: Sensor cycle with 1 ppb H2S. Cycle sub-section are as follows:
1 = Baseline calibration
2 = Span Calibration
3 = Sample
4 = Sample with H2S filter

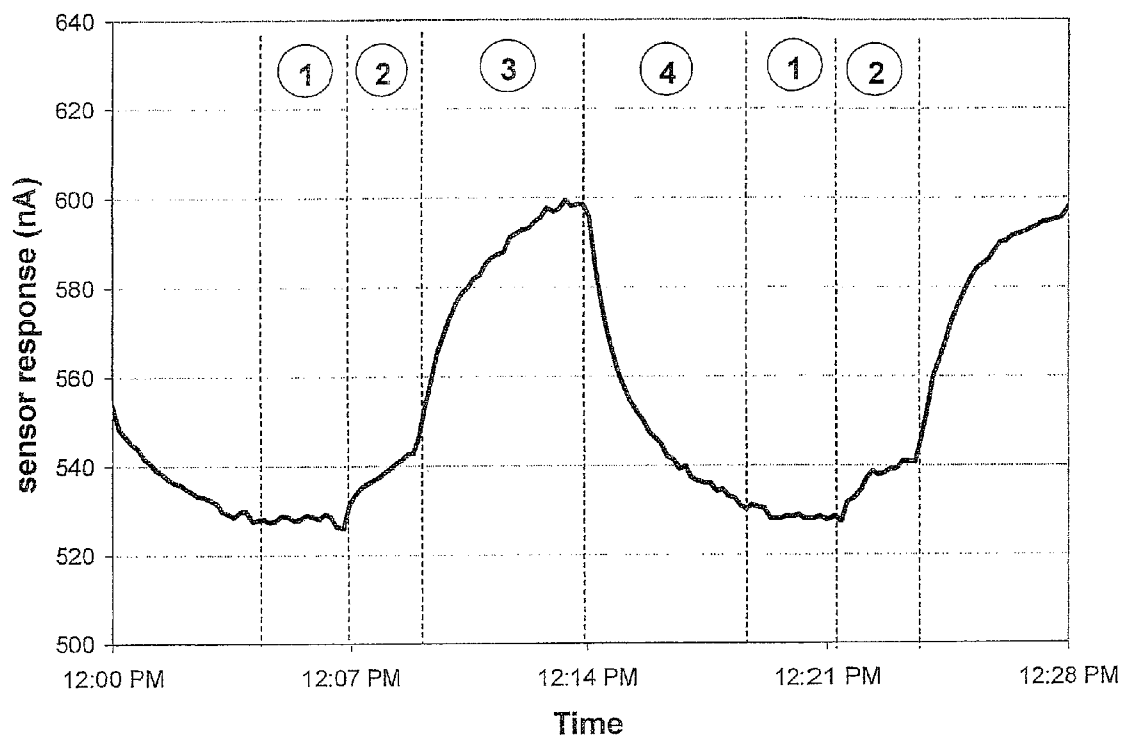
Figure 8: Sensor cycle with 8 ppb H2S. Cycle sub-section are as follows:
1 = Baseline calibration
2 = Span Calibration
3 = Sample
4 = Sample with H2S filter

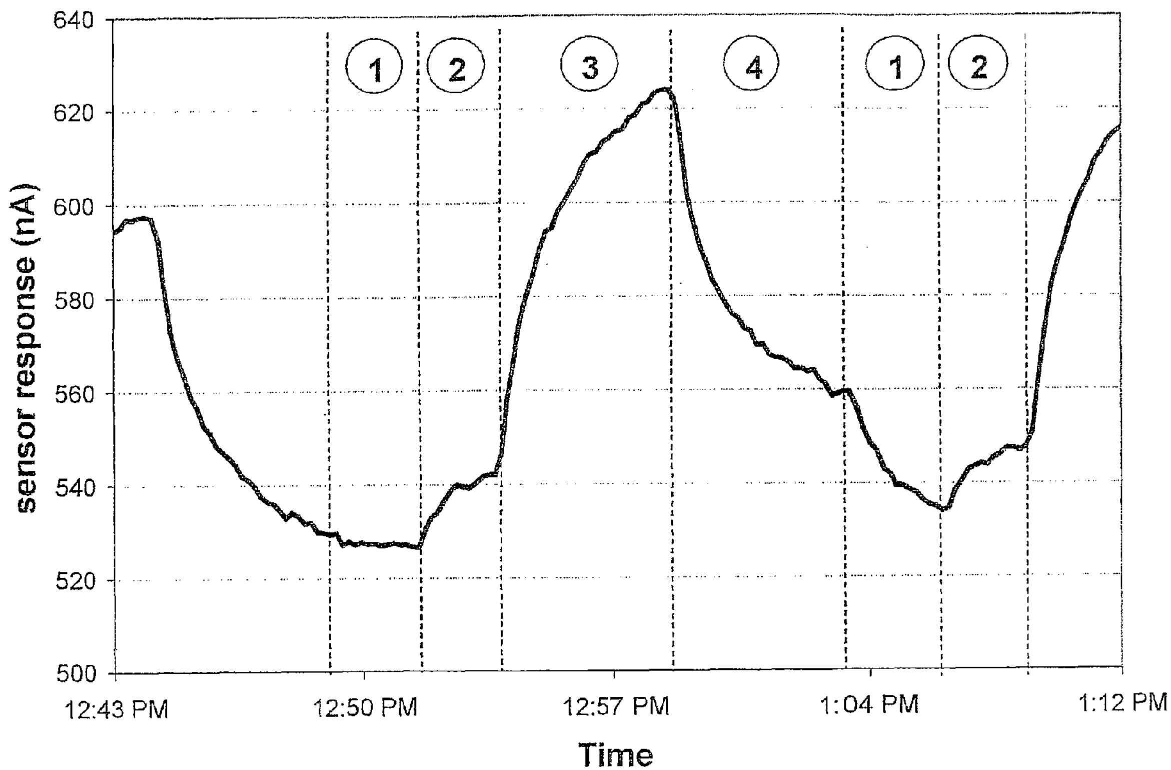
Figure 9: Sensor cycle with 8 ppb H2S and 15 ppb methyl mercaptan. Cycle sub-section are as follows:
1 = Baseline calibration
2 = Span Calibration
3 = Sample
4 = Sample with H2S filter

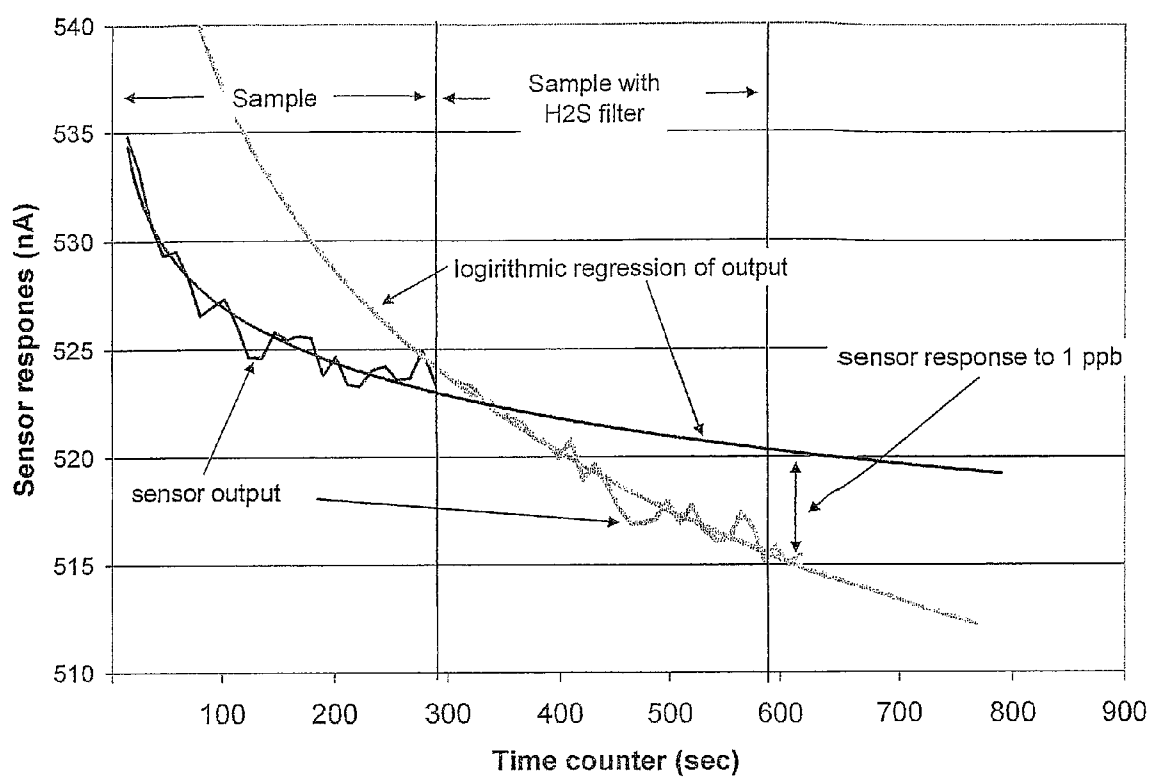
Figure 10: Quantifying sensor response

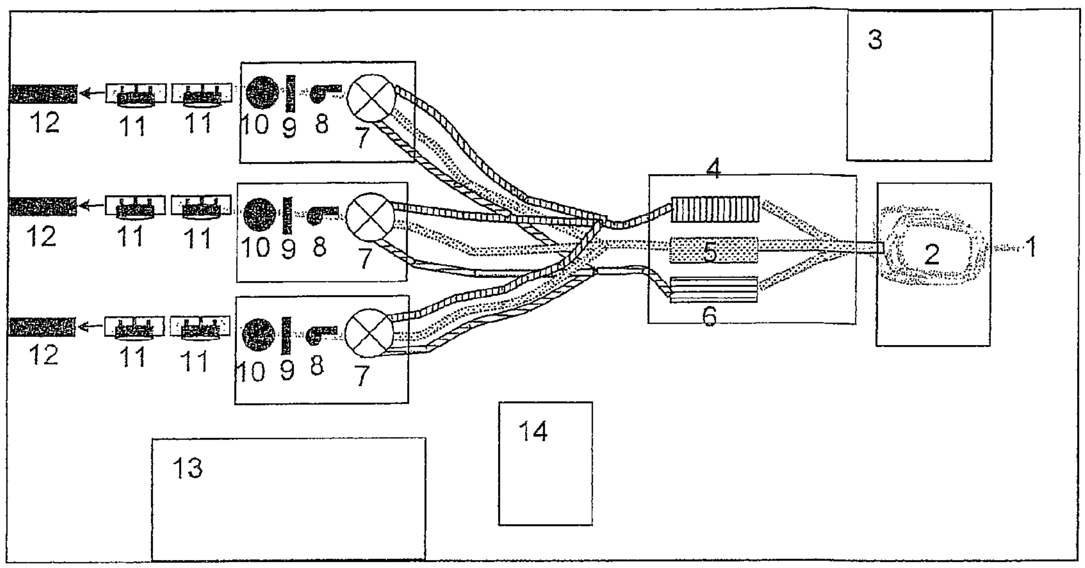
Figure 11: Schematic layout of monitor
1 :Sample inlet
2: humidity conditioning tube
3; Calibration module
4: H2S filter and stream
5: Sample stream
6: Zero filter and stream
7stream switching valve
8: Sample pump
9: Flow Sensor
10: H2S source
11: Sensors
12 exit filter
13: controller and memory
14: battery module

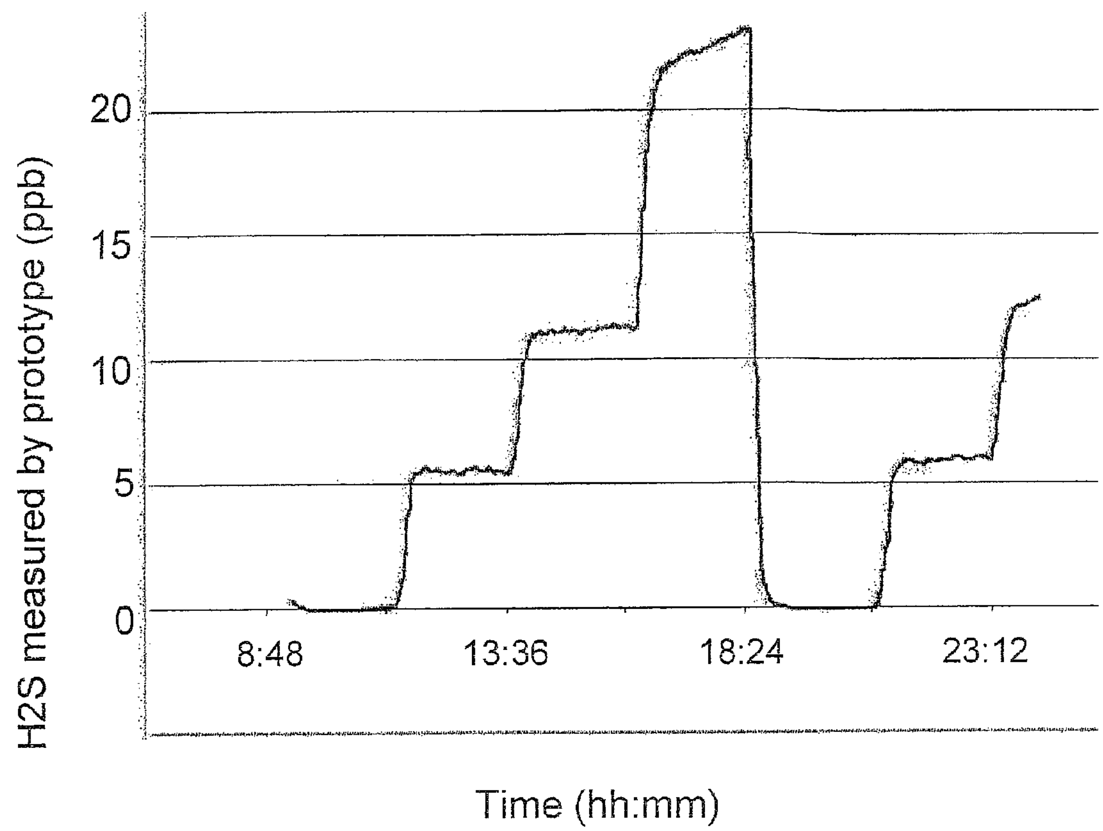
Figure 12: Sample of prototype output measuring 0, 6, 12, and 24 ppb H2S in the laboratory

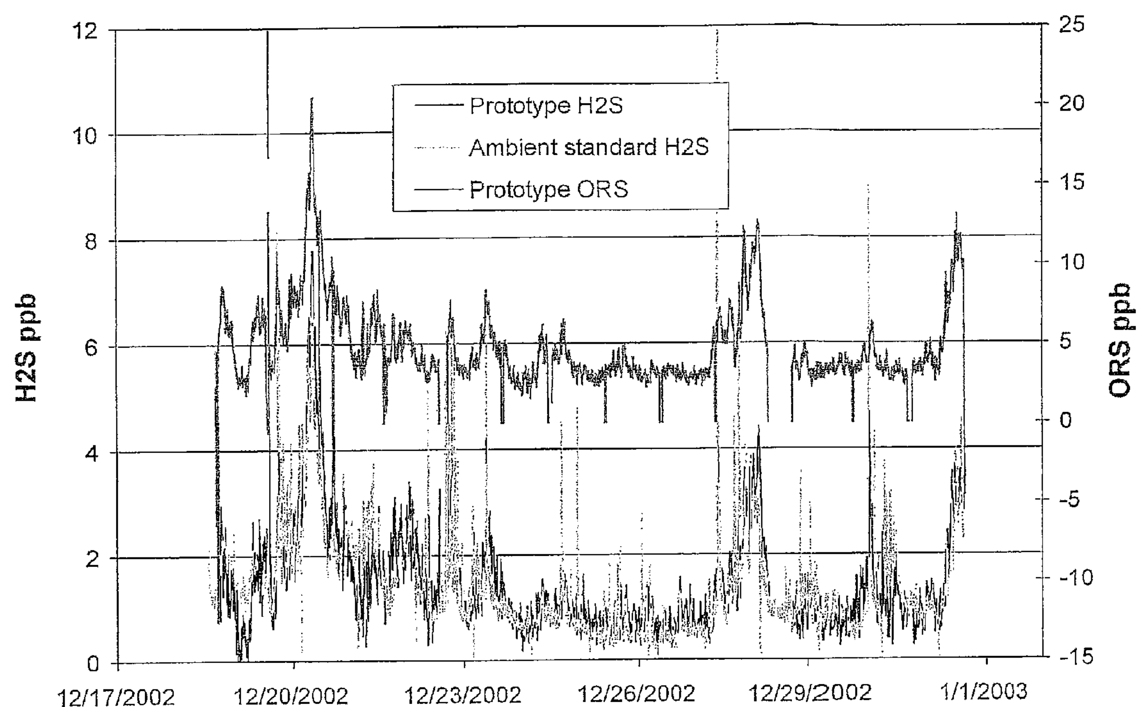
Figure 13: Results of field test with prototype monitor and Alberta Environment ambient station monitor.

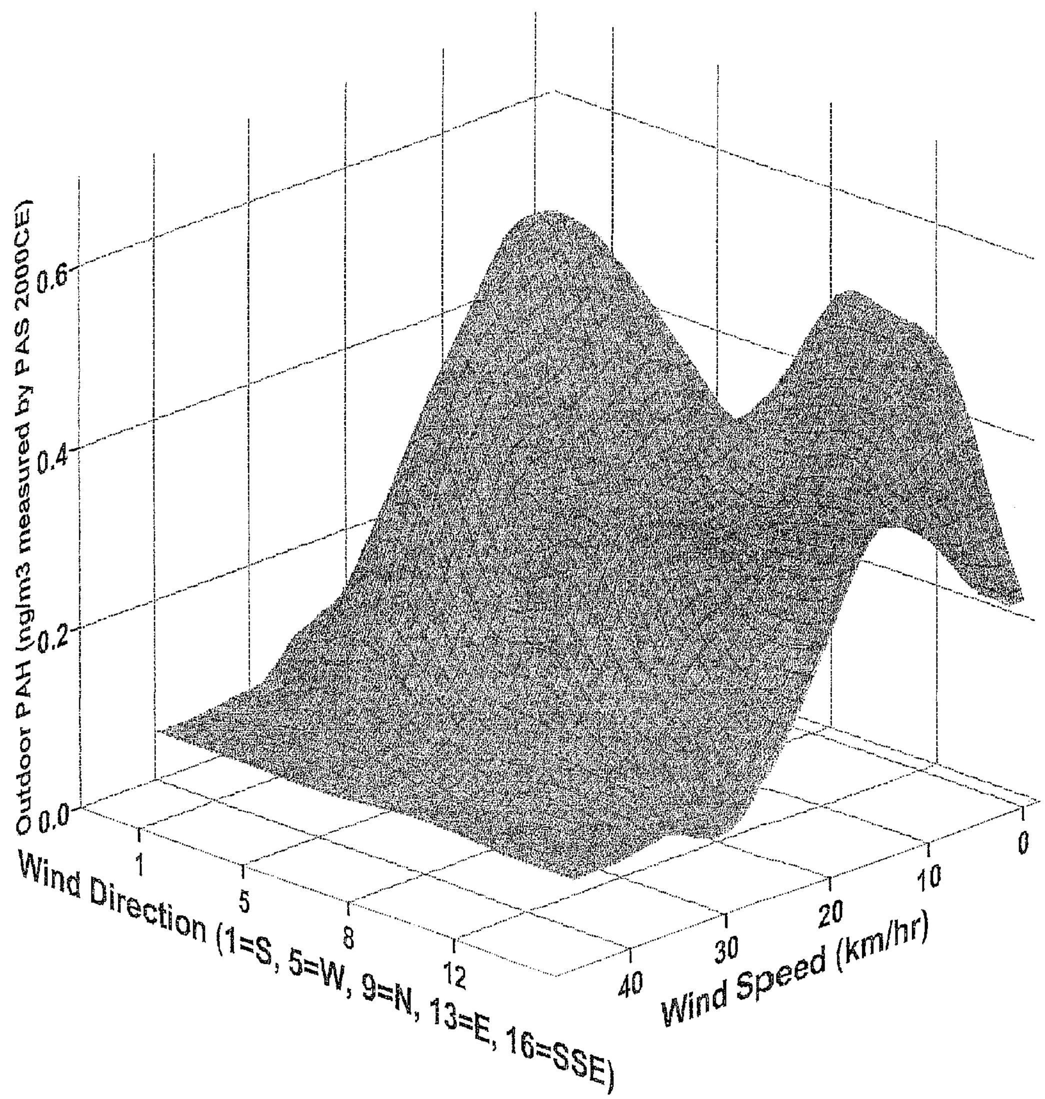
Figure 14: Surface representing mean real-time measures of PAH levels outdoors compared to wind speed and direction.

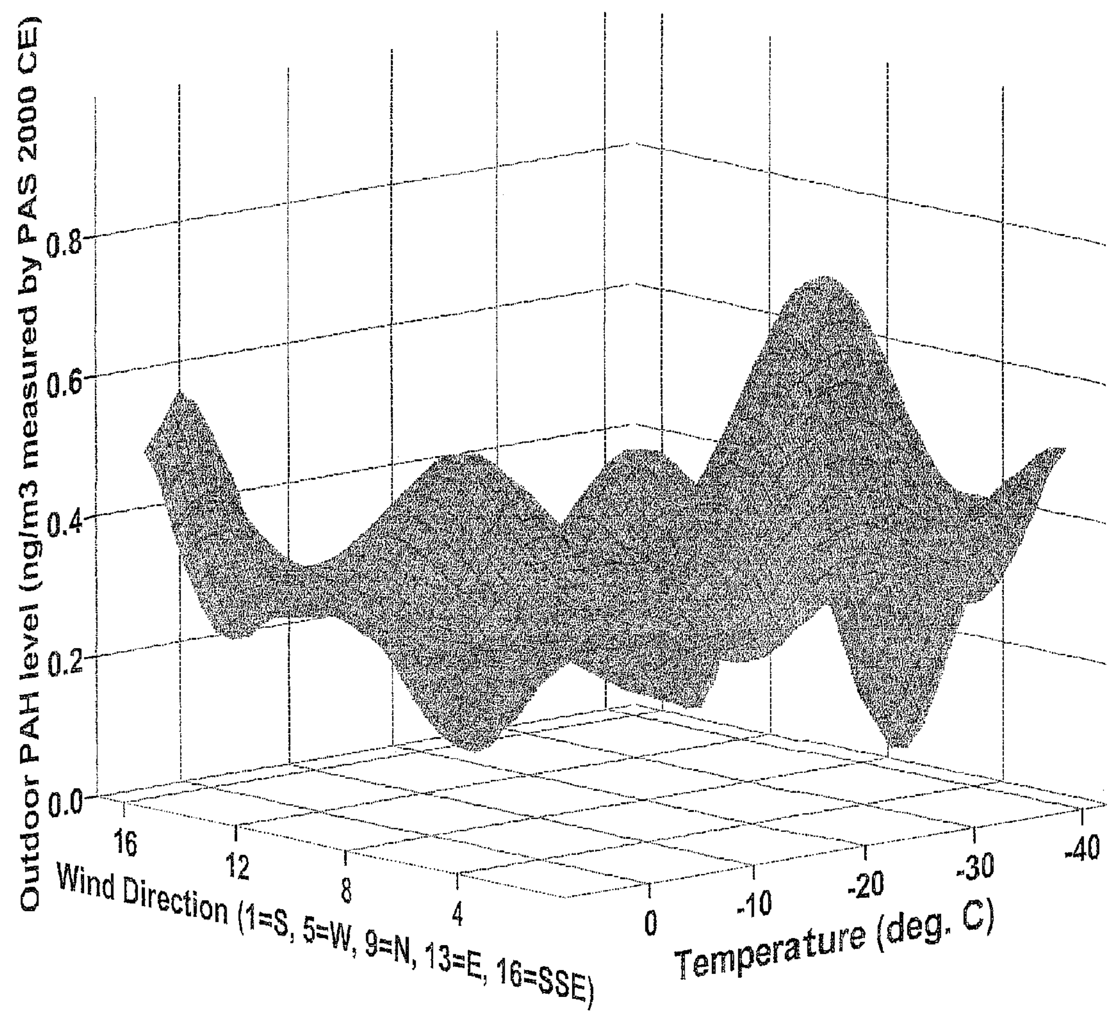
Figure 15: Surface representing mean real-time measures of PAH levels outdoors compared to wind direction and for temperature.

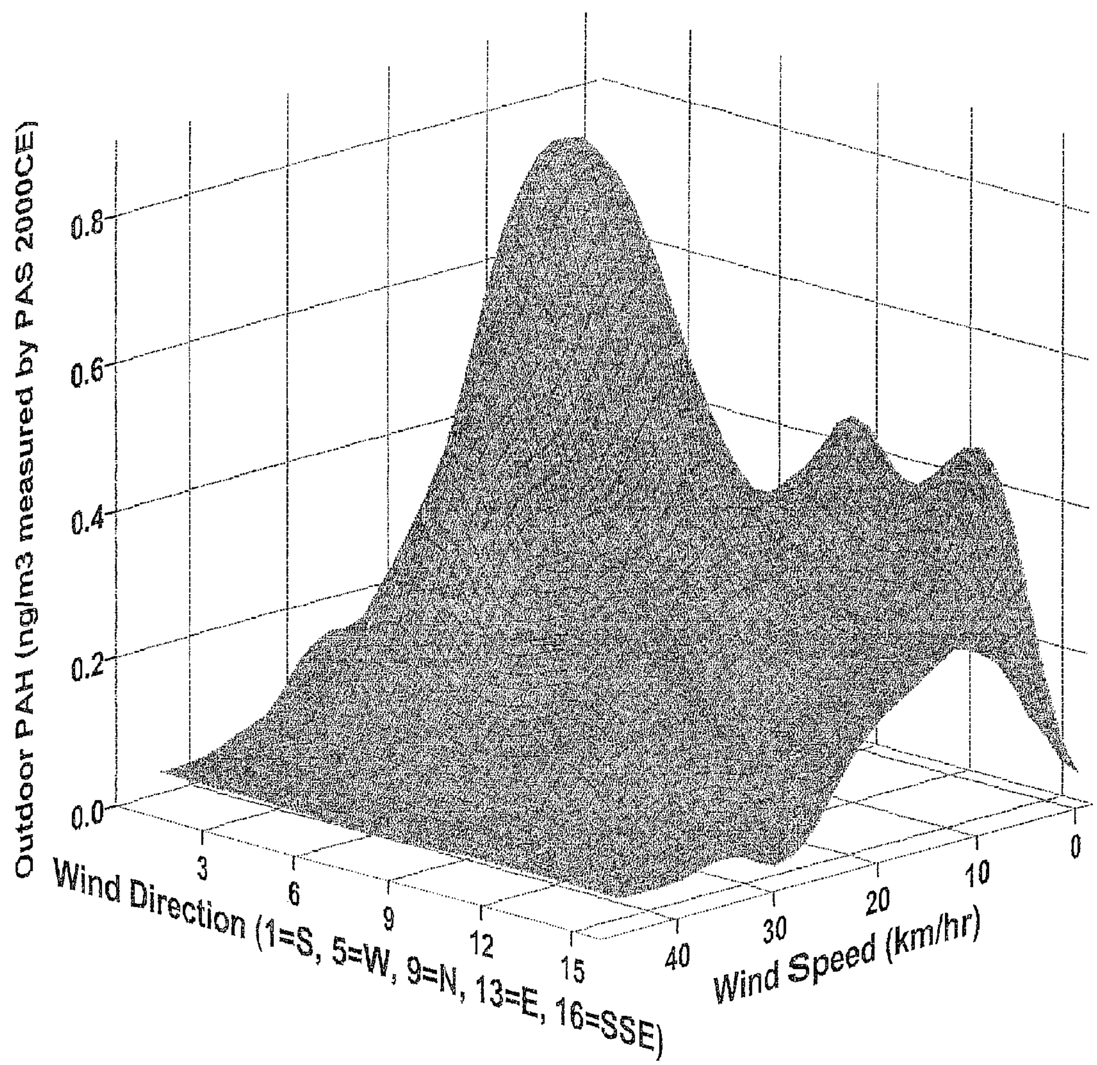
Figure 16: Surface representing mean real-time measures of PAH levels outdoors compared to wind speed and direction for temperatures less the -15 C.

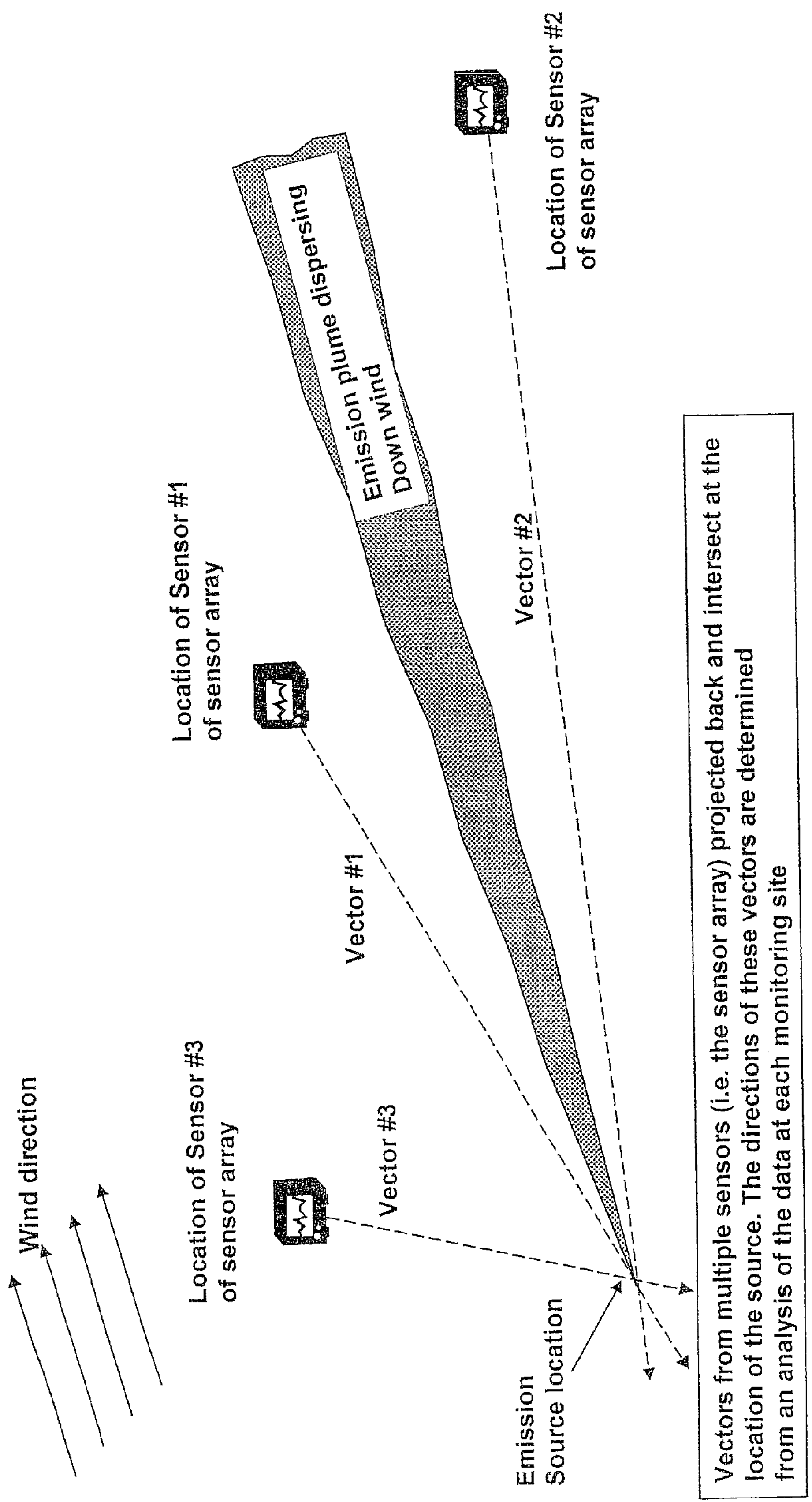
Figure 17: Figure showing sensor array and source location technique.

INNOVATIVE GAS MONITORING WITH SPACIAL AND TEMPORAL ANALYSIS

CROSS REFERENCE TO RELATED APPLICATIONS

This application claims the benefit of provisional application No. 60/481,266 filed Aug. 20, 2003.

FIELD OF THE INVENTION

The present invention relates to gas monitoring, and more particularly to methods for determining sources of emissions.

BRIEF DESCRIPTION OF THE DRAWINGS

Reference will now be made to the accompanying drawings which show, by way of example, embodiments according to the present invention and in which:

FIG. 1 shows in graphical form exemplary data collected over a three day period;

FIG. 2 shows in graphical form data corrected for sensor baseline response and overlaid on the data of FIG. 1;

FIG. 3 shows in graphical form data corrected for changing sensor sensitivity over time;

FIG. 4 shows in graphical form monitor predictions when multiple sensors are averaged;

FIG. 5 shows a plot of percent relative standard deviation versus H2S concentration;

FIG. 6 shows a plot of the output of five sensors working in a synchronized mode of operation;

FIG. 7 shows a plot of a sample cycle for one sensor exposed to H2S;

FIG. 8 shows a plot of a sample cycle for a sensor exposed to another concentration of H2S;

FIG. 9 shows a plot of the comparison between the H2S filter mode and the baseline calibration;

FIG. 10 shows a plot of logarithmic fitted curves for sensor outputs;

FIG. 11 shows in schematic form a monitor according to an embodiment;

FIG. 12 shows a plot of an exemplary measurement cycle;

FIG. 13 shows a plot of another exemplary measurement cycle;

FIG. 14 shows in graphical form an exemplary three dimensional plot for measurements;

FIG. 15 shows in graphical form another exemplary three dimensional plot;

FIG. 16 shows in graphical form another exemplary three dimensional plot; and FIG. 17 shows an exemplary arrangement for a sensor array and source location method according to an embodiment.

DETAILED DESCRIPTION

The present invention relates to the monitoring of gas concentrations possible in very low ranges (i.e. low ppb and even ppt ranges) and especially use thereof in environmental monitoring, exposure assessment, bomb detection, and health studies. The invention can use a spacial and temporal assessment of gas concentrations that enables the sources of the gas in question to be located and identified which is useful in environmental and health field but can also be applied to other fields an example of which is detecting and locating explosives. This technology uses small, light weight, and low power components that allow for the monitor to be portable and even worn on a person as a personal monitor. This technology can be used in stationary monitors as well.

This technology is a platform that can be tuned and adjusted to measure many different gases including but not limited to H2S, ammonia, SO2, NO2, and others even compounds that are related to explosives.

This personal or portable monitor can include a device that tracks spacial position for example a GPS device or a tracking system that works based on a receiver receiving a signal from stationary transmitters of known location and triangulating the position of the monitor based on the signals received.

This monitor will include a means to record and store the gas concentration, special position and time of the readings. This monitor can be fitted with the provision to transmit the data collected either by a wire connection or a wireless transmitter to a computer station or other similar device. The data can then be stored and archived and analyzed; using algorithms designed to watch and notify if conditions of concern arise. These algorithms can include spacial and temporal analysis of the gas concentrations (in effect mapping of the gas concentration) that may provide evidence of the sources of the gases being measured (i.e. locate the sources).

Several monitors can be downloading (by wireless transmissions if needed) to a single database that is updated and maintained with the algorithms applied to constantly compare the new data to previously collected data and watch for anomalies that can identify undesirable conditions. For example, multiple mobile monitors can measure and transmit concentration and position information to a central computer which combines and analyzes the information and can characterise the gas concentrations over an area that is useful for exposure, environmental and health concerns. The information can also identify and locate sources of the gas in question which is valuable in trying to reduce the concentration of the gases by locating and eliminating the source. For example this would be useful in industrial operations were some fugitive emission of gases go unnoticed by the standard air monitoring networks. This method would be useful in many other fields including the detection and locating of explosive devices within apartment buildings or outdoor environments including public areas.

The work done to prove the concept of this invention is in two major areas, first the gas monitor, and secondly the spacial temporal gas concentration analysis.

The following is a description of a monitor that uses electrochemical cells that have a low noise to signal ration which makes them very sensitive. The cells used in the prototype are made by TSI but other similarly sensitive cells would work the same. The prototype was tuned to and tested on H2S gas but it can be tuned to measure other gases. The present prototype superimposed a gas concentration of the target gas on the sensors and generates this gas using electrochemical cells (made by ACD) but could use other electrochemical cells or methods to generate the gas on the monitor.

The super imposed gas does not have to be the same as the gas to be measured. A different gas could be used to react with and eliminated the effect of an interfering gas, or react with the target gas and form a different compound which is then measured on the sensitive sensors. Similarly a different gas could be introduced into the sample stream that forms a compound on the surface of the sensors that will react more readily with the target gas and provide a stronger signal. In effect, the superimposed gas can be used to isolate or amplify the signal from the target gas.

The development of the invention has used three prototypes (three phases) to prove the concept of measuring low concentration of gases on a small light weight monitor that could be portable or personally worn. This development has targeted H2S and other reduced sulphur compounds but the same methods could be used to measure other gases. The following describes the development. It is possible to replace individual components of these prototypes with other things not mentioned that perform the same function.

The methodology was developed to monitor low ppb (parts per billion) air concentrations of H2S in real time with small light weight equipment adaptable to portable or even personal monitors.

In the first phase an investigation of monitoring techniques determined that highly sensitive electrochemical sensors (amperametric sensor) were the most promising technique given their small size and low power requirements.

The difficulties with the electrochemical sensors are that they respond to many compounds (lack of selectivity) and the response to low ppb levels of H2S is not consistent. While they are sensitive enough to respond to 1 ppb H2S the response is not consistent and varies with humidity, sensor baseline, and recent exposures to H2S. The sensor responds to H2S concentrations with a measurable increase in current that rises logarithmically requiring hours to reach to a stable output and similar time to return to the pre exposure baseline levels. During this logarithmic increase or decrease in current measured the sensor sensitivity to H2S changes making it difficult to predict H2S concentrations.

The methodology developed incorporated the following techniques to address the complicating factors: Impose bias voltage (+300 mv) on sensor to reduce sensor response to other reactive gases (phase 1); Frequent Baseline correction (phase 1); Frequent calibration cycles (to measure sensor sensitivity) (phase 1); Using multiple sensors to improve accuracy and eliminate outliners (phase 1); Superimposed H2S concentration on the sample (to maintain sensor sensitivity) (phase 2); Gas specific filters to further isolate the sensor's response to H2S (phase 2); Logarithmic curve fitting to measure sensor response (phase 2). The first phase of the investigation used a prototype monitor with the capability to adjust bias voltage, baseline correct, sensitivity correct, and used multiple sensors. This prototype had limited data logging capability only taking readings every ten seconds. The following information was obtained from the investigation.

FIG. 1 shows data collected over three days comparing the H2S concentrations measured by a commercial ambient monitor versus a prototype monitor using electrochemical sensors (calibrated with the average sensitivity over the time period). The figure shows that overall the prototype monitors response is correlated with H2S concentrations but there are large errors for an individual measure. These errors are due to the sensor sensitivity and baseline drifting during the sample period.

FIG. 2 show data corrected for the sensor baseline response overlaid upon the raw data from FIG. 1. An estimate of the baseline was obtained by periodically running the sample through a zero gas filter and measuring the sensor response. The figure shows there is a great reduction in the scatter of the data particularly at the lower concentrations. There is still considerable error in the measurements at the higher end of the scale.

FIG. 3 shows data that has been corrected for changing sensor sensitivity over time overlaid upon the previous data. There is significant reduction in the error. Sensor sensitivity was determined by periodically exposing the sensor to known concentrations of gas and recording the response (basically recalibration).

FIG. 4 shows the improvements of the prototype monitors predictions when multiple sensors are averaged.

FIG. 5 plots the percent relative standard deviation (RSD, this is the standard deviation of a group of data points at a given H2S concentration divided by the mean of those points) versus the H2S concentration. The figure shows the improvements in the prototype monitors precision resulting from the application of the methodologies discussed in this section. An estimate of the detection limit of the monitor is obtained by reading the H2S concentration when the fit lines cross the 33% RSD (this is related to three standard deviation of the instrument background noise which is a commonly used by laboratories as the limit of detection). The detection limit of the prototype operating with baseline correction, sensitivity correction, and multiple sensors is roughly 2 to 3 ppb.

In the second phase a second prototype was constructed with the following improvements: 1. The capability to generate a H2S concentration to superimpose on the sample 2. The capability to quickly change the superimposed H2S concentration for calibration purposes by adjusting the flow rate which increases the concentration of the superimposed H2S concentration which allows for a simple method to check sensor sensitivity providing a convenient calibration method 3. A record rate of three readings per second The monitor continuously cycles the sensors through the following four modes of operation: 1. Baseline calibration 2. Span calibration 3. Sample reading 4. Sample reading with an H2S filter Combining the information from the four modes provides a good estimate of the H2S concentration as well as other reactive sulphur compounds. The monitor has grouped the six onboard sensors into groups of two and offset the modes of operation so that there is always a set of sensors reading a sample (maintaining a continuous monitor).

The following sections summarize the findings of the investigation of the second prototype.

FIG. 6 shows the output of five of the sensors working in synchronized modes of operation and being exposed to varying concentration of H2S and methyl mercaptan (a common interfering gas that can also be detected by the human nose at low concentrations). The figure shows the similar magnitude of response between the sensors. This similarity in response is a result of a 25 ppb superimposed H2S concentration that maintains the concentration of the secondary reaction products on the sensor surface and provides similar sensor sensitivities.

The capability to quickly change the superimposed H2S concentration for calibration purposes and the increased recording rate has enable the monitor to operate in short cycles that help to eliminate noise and allows for better interpretation of the sensor output. FIG. 7 is a sample of a cycle for one sensor exposed to roughly 1 ppb of H2S. The modes of the cycle are listed on the figure. Comparing the output during the sample modes and the H2S filter mode is an indication of the response to 1 ppb. Similarly in FIG. 8 the response to 8 ppb is shown. In FIG. 9 the comparison of the line during the H2S filter mode and the baseline calibration is an indication of 15 ppb methyl mercaptan that was present along with 8 ppb H2S.

The cycles used here are examples of how they can be used to measure gas concentrations. The ordering of the parts of the cycle can be changed and not all the parts of the cycle are required to measure the gas concentration.

FIG. 10 demonstrates how logarithmic fitted curves will be used to fit to the output and compared to quantify sensor output. The first part of the figure is the sample mode while the second part is the H2S filter mode the arrow indicates the sensor response.

In the third phase the product is a monitor for H2S that enable personal/portable monitoring with a low ppb detection limit. In addition to H2S, the monitor also estimates a concentration of a group of other reduced sulphur compounds (ORS) having odours that are sometimes mistaken for $H_2S$.

The monitor uses highly sensitive electrochemical sensors (also called amperametric sensor) because of their small size and low power requirements. The difficulties with the electrochemical sensors are that they respond to many compounds (lack of selectivity) and the response to low ppb levels of H2S is not consistent. While they are sensitive enough to respond to 1 ppb H2S the response is not consistent and varies with humidity, sensor baseline, and recent exposures to H2S. The sensor responds to H2S concentrations with a measurable increase in current that rises logarithmically requiring hours to reach a stable output and similar time to return to the pre-exposure baseline levels. During this logarithmic increase or decrease in current measured the sensor sensitivity to H2S changes making it difficult to predict H2S concentrations.

A methodology was developed to address the complicating factors using the following techniques: Imposed bias voltage (+300 mv) on sensor to reduce sensor response to other reactive gases; Frequent Baseline correction; Periodic calibration (to measure sensor sensitivity); Using multiple sensors to improve accuracy and eliminate outliners; Superimposed H2S concentration on the sample (to maintain sensor sensitivity); Gas specific filters to further isolate the sensor's response to H2S; Logarithmic curve fitting to measure sensor response. The schematic diagram in FIG. 11 illustrates the layout of the components used to implement the methodology developed. The monitor uses two special electrochemical sensors with bias voltage adjustment on each of three channels. The valves on each channel switch rapidly (15 sec. to 5 min.) between drawing an air sample; an air sample with the H2S filtered out, or an air sample with all contaminants removed for a baseline reading. The H2S and ORS signals are calculated based on the difference in the sensor output between the different samples. Logarithmic curve fitting is use to quantify the differences in sensor output as illustrated in FIG. 10 for a sensor exposed to 1 ppb H2S. Low levels of H2S are generated in each channel and superimposed on the sample with a controlled flow loop. Exit filters remove any H2S that has been added before the air leaves the monitor. Because low humidity can damage the sensors a humidity module at the intake will increase moisture in the sample. A calibration module will be connected to the monitor periodically to provide calibration. In between main calibrations, a sensitivity check (quasi calibration) is possible by decreasing the flow which increases the superimposed H2S concentration by a known amount to the sensors.

The methodology described above has been demonstrated in laboratory and field test in a briefcase size prototype. The components (filters, manifolds, circuit boards) displayed in the prototype are much larger than necessary and can be miniaturized so the size and power consumption is suitable for a battery powered personal monitor. Laboratory test results are shown in FIG. 12 for H.sub.2S levels of 0, 6, 12, and 24 PPB generated in a chamber in the laboratory. Note the changes in concentration in the chamber were associated with the transition periods shown in the figure and do not reflect the response time of the monitor. Data from ten days of field-tests where the prototype was collocated with an ambient monitor at an Alberta Environmental Protection station is shown in FIG. 13. The field and laboratory test data shows good agreement to the expected H.sub.2S, concentrations in the low ppb range. The field test data in FIG. 13 also shows predicted levels of the ORS present at the site.

The portable version of the monitor includes three channels providing continuous measurements of H.sub.2S, ORS, and baseline levels. Size and weight can be minimized in the personal monitor by using only one channel, which would provide an intermittent measure of H2S and ORS rather than a continuous measure.

The unique aspects of low detection limit, light weight, and low power operation will compete with existing monitoring systems and open new markets in areas considered impractical at this time.

The portable monitors will allow government agencies to respond to public complaints by taking measurements to determine the level of $H_2S$ and ORS. The personal monitor will provide information for health assessments and could be used to provide concentration data for studies that look at the impact on human and animal life. Industries would also be interested in the monitors for the reasons above as well as the benefits gained from collecting this air data with an added spacial/temporal analysis which can locate sources of contamination.

Innovation in technology can precipitate profound changes in practices and approaches to problems. Low ppb air quality monitoring has been characterized by permanent ambient monitoring stations that are costly and lack flexibility in addressing public concerns about air quality and health. A portable/personal monitor with ambient monitor detection limits opens the possibility of answering the questions the public is raising that are impractical to address with the current monitoring regime and provide valuable solution to other questions that industries haven't considered yet. With respect to the Spacial Temporal Gas Concentration Analysis, the following is the proof of concept. A study of PAH concentrations resulting from a coal fired household furnace is provided to demonstrate the concept of locating sources using spacial and temporal gas concentration (although the PAH are fine particulate bounds they act as a gas for the purposes of this analysis in this instance).

A residence in Vegreville, Alberta was monitored over a five week period for outdoor air concentrations of PAHs and between Feb. 21 and Mar. 28, 2003. Measurements of PAHs were taken using a real-time monitor (PAS 2000 CE PAH monitor, Ecochem Analytics Inc.). The location of the residence monitored was roughly 100 meters east of the location of the coal fired furnace. Meteorological data was obtained from an Environment Canada weather station located roughly 3 km from the residences.

A comparison between the real-time outdoor measures of PAHs and the wind conditions at the time can provide insight into sources of emissions. Studies have shown that weak air movements or calm conditions over cities are correlated with poorer air quality due to pollution not being effectively dispersed. Where no significant point source of PAHs exists in the community or region, the highest concentration of PAHs occur at calm or low wind speeds and the levels decrease to low background levels at high wind speeds.

The real-time PAH and wind data was combined and plotted in FIG. 14 which shows a surface representing the mean of the outdoor real-time PAH levels versus wind speed and direction. The figure shows an increase in the average PAH concentration at elevated wind speeds from the westerly direction indicating a point source in the direction of the coal-fired furnace. A plot of the average PAH levels versus wind direction and temperature shows increased levels when the wind is from the west at temperatures below 15° C. (see FIG. 15). This is as expected given the coal furnace will be producing more heat and higher emission at these low temperatures. Recharting the wind speed and direction diagram using only data with temperature below 15° C. in FIG. 16 shows a dramatic increased impact of the coal furnace at colder temperatures. These figures demonstrate that a point source existed in the direction of the coal furnace and impacted the house monitored when the wind was above 10 km/hr in the direction spanning west-southwest to northwest at temperatures below 15° C. The coal furnace was responsible for the increased PAH levels assuming there were no other significant point sources of products of incomplete combustion in that direction.

This demonstrates how directions of the point sources can be located with real-time concentration data and wind speed and direction data. If data were collected in many locations then the directions provided can be used to pin point the sources location by over laying the directions. With moving monitors the data will be analyzed using a quasi finite element analysis with data from finite geographic areas grouped together and compared with wind speed and direction. Point sources will appear in each finite element similar to the PAH surface in FIG. 16. Lines struck in the direction to a point source from the centroid of several finite elements will cross at the location of the point source. Computer algorithms will be created to perform these tasks on a continuous basis and will be able to determine if new point sources emerge and provide alarms or warning of such.

Wind is not a consideration in indoor environments were concentration data will be mapped and areas of higher concentration will indicate proximity to sources. Temporal patterns of concentrations indoors can also be used to identify sources.

This inventions application to explosive detection as well as many other area is demonstrated here. Sep. 13, 1999 at least 116 people are killed when an eight-story Moscow apartment building is blown up by an explosion. Sep. 9, 1999 an explosion collapses the middle of a nine-story apartment building in a residential Moscow neighborhood, killing 93 people. In both of these cases large bombs were detonated within the buildings. This type of attack could pose a significant threat to America as foreign students or those posing as students could carry explosives in backpacks into apartment buildings unnoticed and build up a bomb weighing tons in a matter of weeks. This large bomb could be easily detonated by a cell phone call from anywhere.

Portable explosive detection devices carried by security personal walking apartment hallways would be able to detect bomb-building activity in the suites. Further, a number of these portable detectors could wirelessly link to a central computer to provide a explosive surveillance system. This system could provide long-term monitoring of a building for the presence of explosive devices or be used for one-time sweeps of a number of buildings. It could also provide surveillance for explosive devices in public where it is difficult to screen people entering different areas.

This approach would locate explosives by identifying anomalies in air concentration of an explosive indicator compound monitored over space and time. The system would compare concentration patterns from one area to another and would track changes in concentration patterns at one location over time. The system would use small portable gas detection monitors (with ultra low detection limits) carried by personnel. The monitors would be tuned to detect a gas that is given off by explosive materials and would transmit the data along with monitor position to a central computer in real time. The central computer would compile the data and generate a map of the characteristic concentrations of the indicator gas over the area in question—such as a large apartment building or public gathering place to be used as reference for future readings. The central computer would use powerful statistical algorithms to analyze the incoming data and identify any spacial or temporal anomalies in the air concentrations that require additional monitor passes or other appropriate responses to confirm the presence of an explosive device.

The effectiveness of such an explosive surveillance system would be limited by the detection limit of the portable monitors. It is not clear what detection limit would be required but it could be in the part per billion or trillion (ppb or ppt) range. A small portable air monitor with this detection limit is not commercially available but it may be possible to develop one.

An environmental issue being addressed by this concept is fugitive emissions of natural gas. Fugitive natural gas leaks are a significant contributor of green house gas (GHG) emissions and are responsible for gas losses estimated at roughly $200 million annually in Canada. A goal of this initiative is to develop a system that measures the amount of fugitive emissions at a facility and localizes the major emission sources within that facility using continuous point measures of methane.

The current approach to measuring overall fugitive natural gas emissions at a facility involves open path optical sensing systems. These systems use a beam of light projected over a long distance (usually along the facility boundary) to measure the air concentrations of natural gas and predict the facility fugitive emission rate (see, for example, FIG. 17). Advanced systems can also locate individual plumes. Alberta Research Council (ARC) has demonstrated the Differential Absorption Lidar (DIAL) technology which can provide two and three dimensional pictures of plumes at a facility boundary (Presentation to PTAC Air Issues Forum. Nov. 19, 2003. http://www.ptac.org/env/dl/envf0303p11.pdf).

The current approaches to localize fugitive emission sources use hand-held instruments that personnel carry through a facility either measuring the size of leaks or looking for leaks. The size of a leak is determined by measuring natural gas concentrations in the immediate vicinity of the leak (i.e. sniffing a flange). Currently, leaks are located by sniffing all potential locations. Recent advances will see hand-held sensors (open path optical sensors or infrared cameras) that can be used to locate plumes from leaks several meters from the monitor.

These current methods use high-intensity data collection over a short period of time and provide a snap shot of the fugitive emission at a facility. The innovation in the proposed technology will both localize fugitive sources and characterize overall site emissions in a continuous manner using long-term, low intensity data collection combined with sophisticated data analysis.

The purpose of the new technology is to characterize overall facility emissions and localize the sources of these emissions using point measures combined with a sophisticated data analysis. This concept would result in a continuous surveillance system that consists of a monitor feeding data to a computer that updates a fugitive emission map of the facility. The crux of the idea is that a sophisticated analysis of continuous point measures is a more efficient and effective method to characterize and reduce fugitive emission than the current alternatives of short duration facility audits using systems like the DIAL laser or handheld sensor carried by personnel.

The only other alternative that attempts to do both source localization and overall site fugitive emission measures is the DIAL system demonstrated by ARC. The one DIAL system planned for Western Canada would move between sites and provide snap shots of plume profiles at the facility perimeter. The continuous nature of the proposed system is a significant improvement over the DIAL system in that it will better support continuous improvement strategies at facilities. Facility managers and operators will have continuous feedback of the impact changes in operational practices and procedures have on fugitive emission which will be a powerful tool in continuous improvement strategies.

If adequate resolution of leak location is achieved, the proposed technology could also be an alternative to the hand-held leak location devices currently in use. These hand-held systems depend on personnel to move the monitor into the plume for measurement with the position of the monitor identifying the leak location. In contrast, the proposed technology relies on the wind to carry the plume from the leak location to the monitor, which is stationary, and traces back to the location of the leak using computer algorithms to analyze the wind information. Again, the crux of this approach is that it will be more effective (and less expensive) to leave a monitor running in a fixed location and have a computer perform a complex analysis of the data than it is to have personnel move the monitor around with little analysis of the plume. An important advantage of the proposed system is that it performs a continuous exhaustive surveillance of the entire facility where the hand monitors only finds leaks where and when they are looked for, leaving leaks in unsuspected locations undetected. As a possible limitation, the proposed system will provide a continuous measure of the leakage rate from a building but will not likely be able to resolve leak location within the building.

The technologies current stage of development is a conceptual field prototype. The fundamental concepts of the technology have been demonstrated in the field with other contaminants but have not been attempted on natural gas. The fundamental concept of, locating contaminant plumes with point measures has been demonstrated in previous work identifying emissions from a coal fired furnace. The attached FIG. 16 taken from an unpublished study by the applicant shows the average levels of point measures of PAH concentrations plotted with wind speed and direction. This figure represents five weeks of data taken from a location near a house that was burning coal for heat. The contaminant plume shows up on the figure as a spike in concentration with wind from the west (the direction source) at 20 km/h. The figure shows how sources can be located using point measurements rather than open path optical sensing systems. This same approach will be able to locate the plumes of natural gas fugitive emissions.

This project will determine the sensitivity (i.e. how small of a leak can be located to what resolution) of the surveillance system. Additionally, the relationship between field monitor performance and system sensitivity will be determined (i.e. what quality of monitor do you need to make an effective system).

The market potential for the technology is a surveillance system for every gas plant A surveillance system can be available soon after the project is complete (or even before) if it uses commercially available monitors and manual data analysis (performed offsite). With experience, the data analysis will be streamlined and software will be developed to completely automate the analysis component of the system and provide on-site data analysis in real time. Given a sufficient market driver, the ideal surveillance system that uses a low maintenance monitor with on-site real time data analysis could be available in two years.

Traditional air dispersion modeling starts with a source of known character and predicts down-wind plume concentrations under assumed meteorological conditions. This concept endeavors go in the opposite direction by measuring plume concentrations and predicting source characteristics (location, size, etc.). Algorithms developed to solve this puzzle can be readily applied to data collected at facilities to provide valuable information to reduce fugitive emissions.

What is claimed is:

1. A method for determining a source of an emission, said method comprising the steps of:
- sampling, measuring and recording concentrations of the emission at a plurality of points using a sensor that is moving through a defined space;
- tracking and recording the sensor's position at each sampling;
- mapping the location of a plurality of sampling positions and associated concentration measurements; and
- determining the emission source based on said mapping.

2. The method of claim 1, where the defined area space comprises a space out of doors, and tracking comprises determining the location of the sensor with a GPS device.

3. The method of claim 2, where the defined space comprises a space in a building, and tracking comprises receiving a signal from a transmitter associated with said sensor to determine the location of the sensor.

4. The method as claimed in claim 3, wherein said emission comprises a compound indicative of an explosive.

5. A method for determining one or more characteristics associated with a source of an emission, said method comprising the steps of:
- sampling and measuring concentrations of the emission at a plurality of points using a sensor, wherein said sensor moves through a defined space;
- tracking and recording the sensor's position at each sampling;
- mapping the location of a plurality of sampling positions and associated concentration measurements; and
- using said mapping to determine the one or more characteristics associated with the emission source.

6. The method as claimed in claim 5, wherein said source characteristics include one or more of a location, elevation, emission rate, and emission rate variability.

7. The method of claim 5, where the defined space comprises a space out of doors, and tracking comprises determining the location of said sensor with a GPS device.

8. The method of claim 7, where the defined space comprises a space in a building, and tracking comprises receiving a signal from a transmitter associated with the sensor to determine the location of the sensor.

9. The method as claimed in claim 8, wherein said emission comprises a compound indicative of an explosive material.

10. The method of claim 1 wherein the emission is related to explosive devices.

11. The method of claim 10 wherein the emission is at least one explosive indicator compound.

12. The method of claim 1 wherein the emission is a health concern.

13. The method of claim 5 wherein the emission is related to explosive devices.

14. The method of claim 13 wherein the emission is at least one explosive indicator compound.

15. The method of claim 5 wherein the emission is a health concern.

16. The method of claim 5 wherein the emission is related to explosive devices.

17. The method of claim 16 wherein the emission is at least one explosive indicator compound.

18. The method of claim 5 wherein the emission is a health concern.

* * * * *